United States Patent
Arcaini et al.

(10) Patent No.: US 8,149,115 B2
(45) Date of Patent: Apr. 3, 2012

(54) EXPLOSIVE DETECTION PORTAL

(76) Inventors: Gianni Arcaini, Jacksonville, FL (US); Larry Strach, Jacksonville, FL (US)

( * ) Notice: Subject to any disclaimer, the term of this patent is extended or adjusted under 35 U.S.C. 154(b) by 338 days.

(21) Appl. No.: 12/411,745

(22) Filed: Mar. 26, 2009

(65) Prior Publication Data
US 2010/0245081 A1   Sep. 30, 2010

(51) Int. Cl.
*G08B 21/00*   (2006.01)

(52) U.S. Cl. .......... 340/540; 422/89; 73/864.33

(58) Field of Classification Search ........ 73/23.34, 73/23.2, 23.4, 35.14, 23.35, 864.33, 864.81, 73/863.81; 340/540; 422/89, 94
See application file for complete search history.

(56) References Cited

U.S. PATENT DOCUMENTS

| | | | |
|---|---|---|---|
| 4,131,064 A | 12/1978 | Ryan et al. | |
| 4,469,623 A | 9/1984 | Danielson et al. | |
| 5,109,691 A | 5/1992 | Corrigan et al. | |
| 6,840,120 B2 | 1/2005 | Sakairi et al. | |
| 6,840,122 B1* | 1/2005 | Jenkins et al. | 73/864.33 |
| 6,844,546 B2 | 1/2005 | Nagano et al. | |
| 6,872,786 B2 | 3/2005 | Murray et al. | |
| 6,949,147 B2 | 9/2005 | Uziel et al. | |
| 6,967,103 B2 | 11/2005 | Schwartz et al. | |
| 7,307,256 B1 | 12/2007 | Reber et al. | |
| 2003/0041573 A1* | 3/2003 | Davies | 55/385.2 |
| 2003/0085348 A1* | 5/2003 | Megerle | 250/287 |
| 2006/0081073 A1* | 4/2006 | Vandrish et al. | 73/864.33 |
| 2006/0196249 A1* | 9/2006 | Syage et al. | 73/31.07 |
| 2006/0255798 A1* | 11/2006 | Crowley et al. | 324/300 |
| 2007/0056392 A1* | 3/2007 | Cumming et al. | 73/864.33 |
| 2007/0056396 A1* | 3/2007 | Mawer | 73/866 |
| 2009/0248319 A1* | 10/2009 | Call et al. | 702/22 |

* cited by examiner

*Primary Examiner* — George Bugg
*Assistant Examiner* — Edny Labbees
(74) *Attorney, Agent, or Firm* — Lawrence J. Gibney, Jr.

(57) ABSTRACT

This device will allow individuals to pass through explosive detection portals efficiently without undue delay. The airflow from a series of jets will dislodge embedded molecules and direct them to a sensor that will detect the presence of commonly found explosive materials. The molecules that are dislodged will be accomplished by air flow through an air tunnel or portal structure that is not invasive to the person yet allows real time detection of explosive material while not infringing on the privacy of the individual.

10 Claims, 1 Drawing Sheet

EXPLOSIVE DETECTION PORTAL

BACKGROUND OF THE INVENTION

A. Field of the Invention

This relates to the detection of explosive devices in high pedestrian traffic areas. The portal is designed to process as many as 3,000 people per hour such as passengers at transit locations or visitors to sites or arenas. With this system the individuals would walk through portals without long delays normally associated with explosive protection portals.

The system may be deployed at airports, train stations, bus stations, sports arenas, shopping malls, and any areas involving high public concentrations.

B. Prior Art

There are many other prior art references to explosion detection devices and a representative example of this can be found at Kardish U.S. Pat. No. 5,648,047. This is a device with a colorimetric detection of explosives and narcotics. It is a handheld device and is designed to be portable.

Additionally, another prior art reference can be found at Schwartz U.S. Pat. No. 6,967,103, which is an apparatus and method for detecting explosives and substances using polymer and fiberoptic cables to form an image of the target molecule source. There are other devices to remove particles from different structures, including solid state surfaces. An example of this can be found at Uziel, U.S. Pat. No. 6,949,147. There is also laser detection of explosive residue, and this taught is at Haley, U.S. Pat. No. 5,760,898.

Other means to detect explosives include luminescent responses or magnetic responses and both of these methods are taught at Ryan, U.S. Pat. No. 4,131,064.

Other portal detection devices do exist in the prior art and a representative example of this type of device can be found at Jenkins, U.S. Pat. No. 4,964,309. In this reference particles from articles of clothing or objects are dislodged as the person or object passes through the portal. This system involves direct contact with the portal unlike the current device that relies upon air flow to dislodge the particles. The drawback to this system is the relative inefficiency as persons pass through the portal. It is simply not designed to handle large volumes of people because of the necessity of direct contact with the portal.

The great challenge of this type of technology is designing a system where detection is accurate and efficient. Some of the previously cited prior art address the accuracy portion of this type of technology but do not address the efficiency part of the equation. Both of these goals are accomplished by this particular system and method in a way that does not needlessly intrude upon privacy concerns.

BRIEF SUMMARY OF THE INVENTION

The object of this device is to detect the presence of explosives, particularly in high traffic areas such as airport, bus terminals and the like with the least amount of traffic disruption as possible. Additionally, it may also be used to detect the presence of narcotics.

Certain technology does exist that currently addresses this problem and the most frequently discussed prior art technology includes ion mobility spectrometry, back scanner technology and sniffing dogs. While all these technologies are certainly useful, the technology also has certain disadvantages that render the technology impractical in the field.

Generally speaking the preferred system should be highly accurate, quick and easy to maintain and operate and provide real time detection of offending chemicals or other substances. None of the prior art devices have all three characteristics, unlike the current application.

An ion mobility spectrometer (IMS) is a spectrometer capable of detecting and identifying very low concentrations of chemicals based upon the differential migration of gas phase ions through a homogeneous electric field. This type of device has certain delays built into the system because of the time it takes for the ionized molecules to drift through into a tube filled with a viscous gas under the electric field. The identity of the molecule is inferred from the comparison of time versus intensity spectrum to standard information in the system's database. This lack of speed in detection makes this type of technology impractical to use with large public populations.

Back scanner systems are currently being tested and used but have run into various and significant problems as well. Among these concerns are privacy concerns, public perception, and testing time. Back scanner systems have the ability to display and print a form of the person. However, this raises privacy concerns that are typically insurmountable.

Additionally, radiation is used in back scanner systems. While the amount of radiation that used is probably not harmful, the public perception and related stigma cannot be overcome to make the technology useful. The length of time that it takes to scan using this method is longer than would be tolerated for useful applications, particularly for high traffic pedestrian areas. These factors render the technology not feasible on a large scale.

The other major means for explosive detection are sniffing dogs that, of course, require great amounts of time in terms of training and handling the dog as well as the time needed to train the dog handler. Additionally sniffing dogs require constant maintenance and care.

In this application, the inventors have developed a system using a combination of two technologies that will enable accurate and swift explosive detection with minimal upkeep to the system and that does not infringe upon major privacy concerns while achieving maximum performance and reliability. It will also include a method to govern the flow of personnel traffic, which is very important in high pedestrian traffic areas.

The first component of the system is an explosive detector that will use an amplifying fluorescent polymer (AFP). This detector is connected to a portal through which traffic will travel. The explosive detector will utilize a means to amplify fluorescent polymers, which provide realtime detection of explosive vapors. This realtime detection is important for speed and accuracy and because the quantity that can be detected is infinitesimally i.e. as small as a few femtograms or parts per quadrillion.

Conventional fluorescent detection measures a change in fluorescence or light emanating from chromophores or certain isolated molecules that are designed to respond to specific stimulus or analyte. With the convention fluorescent detection, only the chromophores that are directly involved in the analyte interaction undergoes as change in fluorescence.

The first technology or AFP detects a polymer of a given substance and essentially amplifies this polymer into the equivalent of a molecular wire by linking the chromphores thus producing a change in fluorescence in all the molecules. Because the system will greatly amplify the initial detection of small amounts of material this allows the detection at extremely low levels. Even if a small amount of analyte comes in contact with the AFP, a large reaction is evident.

The second technology that is employed with the system is based on chemiluminescence that detects minute traces of the particles and vapors associated with an offending material.

Both sensors will detect military, commercial and even homemade explosives, both solid and liquid including but not limited to nitrates, plastics, peroxides and black powder.

The system will be comprised of a modular air tunnel and each air tunnel will have a multitude of chambers with evenly spaced nozzles to insure complete area of coverage as well as an air intake at the bottom of each of the sides.

A plurality of sensors will be provided and the sensors will be able to detect and identify targets of commonly used explosive devices, including but not limited to, ammonium nitrate, TNT, and nitroglycerin.

As the pedestrian traffic moves through the tunnel a light air flow will dislodge molecules from the clothing or carried items of persons. These molecules will be transferred by the air flow to a sensor for inspection. No direct human interaction occurs with this type of system.

If an offending molecule is detected an alarm that may be visual and/or audio will alert the operator to take corrective action. A simple visual indicator in the form of a green light or red light may be provided. Because the system operates some quickly, the warning will alert the operator in real time so that the operator can then divert a certain amount of traffic to a separate area for closer inspection.

Although explosive detection is discussed, this technology can also be expanded to include the detection of narcotics or any other harmful substance.

NUMBERING REFERENCE

Figure 1:
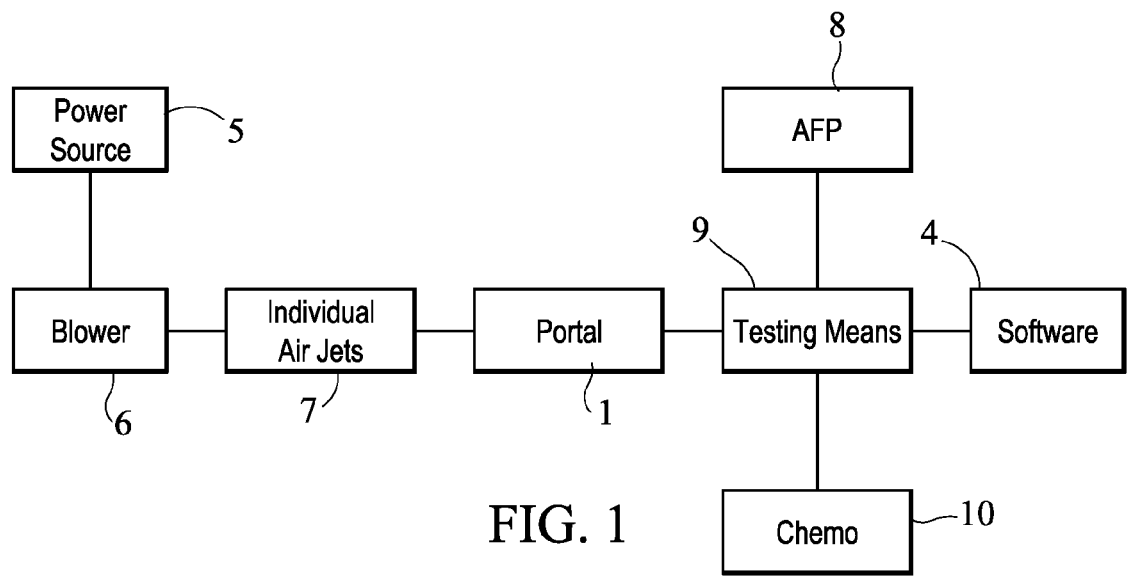
FIG. 1 is a schematic of the components of the system and is for illustrative purposes only.
Figure 2:
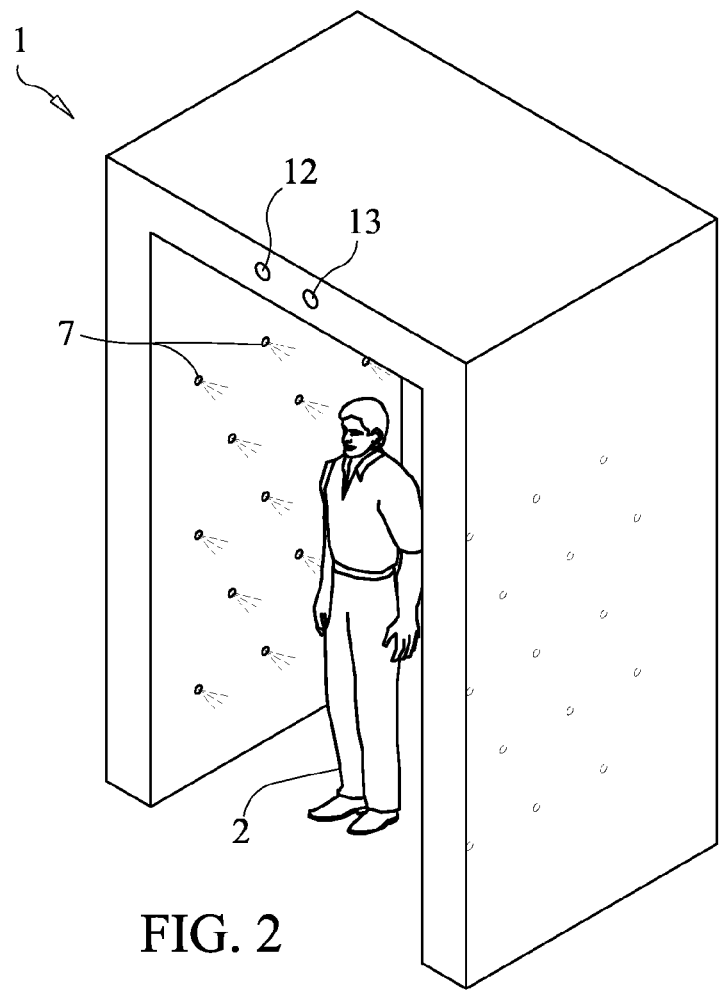
FIG. 2 is a depiction of a person traveling through a portal.

1 Portal
2 Human being
4 Software
5 Power Source
6 Blower
7 Individual Air Jets
8 Amplifying fluorescent polymer technology (AFP)
9 Testing Means
10 Chemiluminescence technology
12 Warning Indicator
13 Go Indicator

DETAILED DESCRIPTION OF THE EMBODIMENTS

This is a method by which two separate and distinct technologies are used to detect very small amounts of explosive residue as individuals 2 pass through an air portal 1 or air tunnel system.

The specific configuration of the portals can be arranged depending on the specific desires or needs of the end user of the system. Although no specific configuration is being claimed, the arrangement should be based on factors to maximize traffic flow with the least amount of delay.

A quantity of air that is produced by a blower 6 and circulated through individual air jets 7 positioned on the portal will be circulated in the air tunnel or portal 1 and dislodge molecules of material that are on a person or the items that a person normally carries. A power source 5 will be provided to provide power for the blower 6 and any other associated equipment.

These dislodged molecules are then collected by sensors 9 that are positioned on the interior surface of the portal for testing. As the individual 2 passes through the tunnel or portal 1, which has a certain predetermined shape, a plurality of air jets 7 will provide a flow of air that will dislodge particles that are embedded in cloth, skin, hair and other objects for sampling by the system. The fan or air jet is not uncomfortable to the individual as he or she passes through the portal and there is no contact with the person or any of the associated equipment.

The dislodged particles are returned through an air intake system located in the portal and direct the molecules to sensors 9 that analyze and identify the molecules from the air contents that have been returned. If any particles are identified that belong to a predetermined group of chemicals of interest, an alarm will be activated. The alarm may include an audible alarm as well as a visual indicator. The alarm may be as simple as the changing of the color of a light from green 13 to red 12 or an audible alarm may also sound.

In addition to the physical portions of the process the system will combine two different technologies to achieve the desired result of detection of offending chemicals.

The first of these technologies is amplifying fluorescent polymer technology 8 or simply AFP, which provides real-time detection of explosive vapors in quantities that are as few as a femtograms or parts per quadrillion. Changes in fluorescence will occur when isolated molecules respond to a specific stimulus.

A chain of isolated molecules form a wire in which the entire chain of molecules in the sequence will be illuminated, causing a large reaction based on a very small quantity of offensive material. With this technology several parts per quadrillion of an explosive or offensive residue will be amplified to alert the user of the possible existence of an explosive in real time.

The second technology that is employed with the system is based on chemiluminescence 10 or chemo that detects minute traces of the particles and vapors associated with an offending material. Stored information about possible offensive material will be stored and when detected by the chemiluminescence will alert the operator.

Once an offending material has been detected, the management portion of the system will trigger an alarm and operators should be able to identify the possible individuals that may have caused the alarm to be triggered. This provides almost instantaneous detection of explosive material.

Once the alarm has been activated either through a lighting system or in combination with an audible alarm, the operator of the system can stop the flow of traffic through the portal 1 and redirect a predetermined number of people to a secondary testing site. While this temporary redirection may inconvenience certain people, the interruption in terms of traffic flow is minimal.

As people pass through the air tunnel or portal, which has a plurality of evenly spaced air jets that provide the air flow, capture and testing, it will insure a complete coverage area as the air is circulated around the interior of the tunnel. The direction and strength of the air flow and the air intake in the system may be adjusted by a variety of means and none are specifically claimed.

Software 4 will be included and will be able to classify predetermined material that are commonly used as explosive material, including peroxide, plastics, ammonium nitrate and nitroglycerin, to name just a few. Other commonly used explosive materials may also be preset into the system for detection purposes.

The inventors claim:

1. An explosive detection portal, which is comprised of:
   a. portal;
   wherein the portal has a predetermined shape;
   wherein the portal has defined sides;
   wherein the portal has a defined top;
   wherein the portal is modular;
   wherein pedestrian traffic moves through the portal;
   b. blower;
   wherein a blower is provided;
   c. power source;
   wherein a power source is provided;
   d. air jets;
   wherein a plurality of air jets are positioned in the portal;
   wherein a stream of air is produced by the blower;
   wherein the stream of air is passed through the plurality of jets;
   wherein the stream of air dislodges molecules from persons traveling through the portal;
   e. sensors;
   wherein a plurality of sensors are provided in the portal;
   wherein the molecules that are dislodged are collected by the sensors;
   f. amplifying fluorescent polymer technology;
   wherein amplifying fluorescent polymer technology is employed;
   wherein the amplifying fluorescent polymer technology detects quantities of offending material;
   wherein the amplifying fluorescent polymer technology creates a strand of a collected molecule;
   said strand is made from a small quantity of material;
   said strand is of a sufficient quantity to be analyzed;
   g. chemiluminescence technology;
   wherein chemiluminescence technology identifies an offending material;
   wherein the chemiluminescence analyzes the strand of material created by the amplifying fluorescent polymer technology;
   h. software;
   wherein software is provided;
   i. alarm;
   wherein an alarm is provided;
   wherein the alarm is activated by certain predetermined preset criteria.

2. The explosive detection portal as described in claim 1 wherein the alarm is further comprised of an audible alarm.

3. The explosive detection portal as described in claim 1 wherein the alarm is further comprised of a visual alarm.

4. The explosive detection portal as described in claim 1 wherein the alarm is further comprised of a visual and an audible alarm.

5. The explosive detection portal as described in claim 1 wherein the amplifying fluorescent polymer technology detects explosive material in the range of femtograms.

6. The explosive detection portal as described in claim 1 wherein the chemiluminescence technology detects the presence of nitrates.

7. The explosive detection portal as described in claim 1 wherein the chemiluminescence technology detects the presence of plastics.

8. The explosive detection portal as described in claim 1 wherein the chemiluminescence technology detects the presence of peroxides.

9. The explosive detection portal as described in claim 1 wherein the chemiluminescence technology detects the presence of ammonium nitrate.

10. The explosive detection portal as described in claim 1 wherein the chemiluminescence technology detects the presence of nitroglycerin.

* * * * *